United States Patent [19]

Löbermann et al.

[11] Patent Number: 5,049,545
[45] Date of Patent: Sep. 17, 1991

[54] INSULIN DERIVATIVES, A PROCESS FOR THEIR PREPARATION, AND THEIR USE

[75] Inventors: Hartmut Löbermann, Weimar; Eric P. Pâques; Norbert Heimburger, both of Marburg, all of Fed. Rep. of Germany

[73] Assignee: Behringwerke Aktiengesellschaft, Marburg/Lahn, Fed. Rep. of Germany

[21] Appl. No.: 323,156

[22] Filed: Mar. 15, 1989

Related U.S. Application Data

[63] Continuation of Ser. No. 14,462, Feb. 13, 1987, abandoned.

[30] Foreign Application Priority Data

Feb. 15, 1986 [DE] Fed. Rep. of Germany ....... 3604868

[51] Int. Cl.$^5$ .................. A61K 37/26; C07K 7/40
[52] U.S. Cl. ............................................ 514/3; 514/4; 530/303; 530/305
[58] Field of Search ............................... 530/303–305; 514/3–4

[56] References Cited

U.S. PATENT DOCUMENTS 4,579,730 4/1986 Kidron ................................ 424/465

FOREIGN PATENT DOCUMENTS 0063109 4/1982 European Pat. Off. .
102827 9/1974 Japan .

OTHER PUBLICATIONS

*The Condensed Chemical Dictionary*, 8th ed., revised by G. G. Hawley, Van Nostrand Reinhold Co., N.Y., 1971, p. 127.

Bruce Alberts, *Molecular Biology of the Cell*, Garland Publishing Inc., N.Y. 1983, p. 212.
"SPDP—Heterobifunctional Reagent", 1978, Pharmacia Fine Chemicals.
Geiger et al., Chem. Ber., vol. 108, 1975, pp. 2758–2763.

*Primary Examiner*—F. T. Moezie
*Attorney, Agent, or Firm*—Finnegan, Henderson, Farabow, Garrett, and Dunner

[57] ABSTRACT

Insulin derivatives of the general formulae I and II

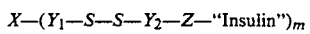

I

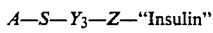

II in which
X is a radical of a physiologically tolerated carbon compound,
$Y_1$, $Y_2$ and $Y_3$ are, independently of one another, a chemical bond or an organic chemical bridge,
S is a sulfur atom,
"Insulin" denotes the biologically active peptidic portion of a natural, semisynthetic or synthetic insulin or an insulin which has been prepared by genetic engineering, or one of its biologically active analogs without the inessential amino group,
Z is an amino group which is inessential for the biological activity of insulin,
A is a hydrogen atom or the radical of a mercapto-containing, physiologically tolerated hydrocarbon compound, and
m is an integer from 1 to 20, agents containing these derivatives, a process for the preparation of these derivatives, and their use for the treatment of metabolic disorders, are described.

4 Claims, No Drawings

INSULIN DERIVATIVES, A PROCESS FOR THEIR PREPARATION, AND THEIR USE

This application is a continuation of application Ser. No. 07/014,462 filed Feb. 13, 1987, now abandoned.

The invention relates to insulin derivatives, to a process for their preparation, and to their use.

Insulin is a polypeptide hormone with a molecular weight of about 6,000 Dalton. Its two amino acid chains A and B are linked together by disulfide bridges. Insulin is synthesized in the form of proinsulin in the β-cells of the pancreas and is secreted as the active form by proteolytic modification with elimination of a moiety called the C-peptide. It carries out an important function in glucose metabolism of mammals. In addition to its hypoglycemic property, it also influences protein and fatty acid metabolism.

It is known that insulin can be used for the therapy of diabetes mellitus. Addition of protamine or spermidine or similar compounds, or addition of zinc salts, results in sparingly soluble insulin derivatives which bring about, for example on subcutaneous administration, a long-lasting reduction in blood sugar. However, side effects may occur with these long-acting depot insulin derivatives. In addition, there is often uneven absorption of these sparingly soluble insulin compounds on s.c. administration.

In contrast to these, soluble insulin acts rapidly. However, the action disappears after a few hours.

Hence the object of the invention is to develop an insulin derivative which can be absorbed intramuscularly or subcutaneously and not only is readily soluble but also does not have, or has to only a diminished extent, the disadvantages of soluble insulin or the long-acting depot insulins.

It has been found, surprisingly, that it is possible by binding insulin to a physiologically tolerated carbon compound to prepare a water-soluble insulin derivative which displays a rapidity of action which is comparable to that of soluble insulin but, in comparison with the latter, has a distinctly longer duration of action resembling that of a depot insulin.

It has also been found, surprisingly, that it is possible by coupling insulin to a proteinase inhibitor to prepare an insulin derivative which is protected from proteolytic inactivation.

It has additionally been found, surprisingly, that it is possible by binding insulin to a physiologically tolerated carbon compound via a disulfide bridge to obtain an insulin derivative which has a defined stoichiometry of insulin to carbon compound.

The invention relates to an insulin derivative of the general formula I

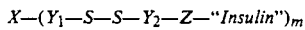

or II

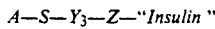

in which
X is a radical of a physiologically tolerated carbon compound,
$Y_1$, $Y_2$ and $Y_3$ are, independently of one another, a chemical bond or an organic chemical bridge,
S is a sulfur atom,
"Insulin" denotes the biologically active peptidic portion of a natural, semisynthetic or synthetic insulin or an insulin which has been prepared by genetic engineering, or one of its biologically active analogs without the inessential amino group,
Z is an amino group which is inessential for the biological activity of insulin,
A is a hydrogen atom or the radical of a mercaptocontaining, physiologically tolerated hydrocarbon compound, and
m is an integer from 1 to 20.

It is possible to use as physiologically tolerated carbon compounds dextran, hydroxyethyl-starch, gelatin or related degraded or crosslinked collagen compounds, polyamino acid compounds, polyoxyethylene or polyvinylpyrrolidone and their derivatives, but preferably a soluble polymer, in particular a polypeptide or protein. The molecular weights are between 500 and $1.5 \times 10^6$ Dalton, but preferably between 2,000 and 500,000 Dalton.

In a particularly preferred insulin derivative, the physiologically tolerated carbon compound which is used is an enzyme inhibitor, especially a proteinase inhibitor, for example alpha$_1$-antitrypsin.

$Y_1$, $Y_2$ and $Y_3$ can be, independently of one another, a chemical bond or an organic chemical bridge, preferably an aliphatic, araliphatic or aromatic hydrocarbon radical in which carbon atoms or hydrogen atoms can be replaced by heteroatoms, especially N, O, P or S.

In a preferred insulin derivative $Y_1$ or $Y_3$ denote a bond, and $Y_2$ contains a —CH$_2$—CH$_2$—CO-group.

Z denotes an amino group which is inessential for the biological activity of insulin, but is preferably the N-terminal amino acid of the B-chain of insulin.

In a particularly preferred insulin derivative use is made of an insulin which has the following N-terminal sequence in the B-chain: Phe(1)-Val(2)-Asn(3)-Glu(4)-His(5)-Leu(6).

Z-"Insulin" denotes a natural, semisynthetic or synthetic insulin or an insulin prepared by genetic engineering, or one of its biologically active analogs. It is also possible to use "insulins" which have undergone N-terminal or C-terminal shortening or extension in the B-chain.

However, the insulin used is preferably one which has as the N-terminal amino acid in the A-chain glycine and in the B-chain phenylalanine.

The insulin which is particularly preferably used is human, porcine or bovine.

"Insulin" denotes the biologically active peptidic portion of insulin without the inessential amino group Z.

It is possible, where A denotes the radical of a mercaptocontaining, physiologically tolerated hydrocarbon compound, to use as such an aliphatic, araliphatic or aromatic in which carbon atoms or hydrogen atoms may be replaced by heteroatoms, especially N, O, P or S. This carbon compound contains from 1 to 50, preferably 1 to 20, carbon atoms, and from 0 to 30, preferably 0 to 15, heteroatoms. In a preferred insulin derivative use is made of mercaptopyridine, cysteine, mercaptopropionic acid, mercaptopyridinecarboxylic acid, mercaptosuccinic acid, glutathione, cysteamine or thiamine. In a particularly preferred insulin derivative use is made of a substituted pyridyl radical, for example 2-pyridylthio. The invention also relates to a process for the preparation of an insulin derivative of the formula I or II, which comprises converting an amino group which is inessential for the biological activity of insulin into a group which contains a mercapto or a mercapto group in protected form, in a compound of the formula III (protective group)—S—Y$_3$—Z—insulin    III and, where appropriate, reacting with a thiol, whereupon a compound of the formula I or II is obtained.

The invention especially relates to a process which is of this type and which comprises selectively providing the N-terminal amino acid of the A-chain of an insulin and the lysine B-29 of the B-chain of an insulin with an amino-protective group, and reacting the N-terminal amino acid of the B-chain of the insulin with a compound which contains a mercapto or the mercapto group in a protected form and which can react with amino groups, by which means the mercapto group is covalently bonded to the N-terminal amino acid of the insulin B-chain, and the amino-protective groups and, where appropriate, the mercapto-protective group are removed and, where appropriate, reaction is carried out with a compound of the formula X—Y$_1$—SH.

In a preferred procedure, initially the amino groups of glycine A-1 and lysine B-29 are selectively protected by methods customary in peptide chemistry, such as, for example, by reaction with t-butyloxycarbonyl active ester derivatives with introduction of the t-butyloxycarbonyl group (Boc), the derivative which is produced being called a Bis-Boc-insulin. In a particularly preferred process use is made of t-butyloxycarbonylhydroxysuccinimide ester (Boc-Osu; Chem.Ber. (1975) 108, 2758-2763). Then a mercapto group is introduced, where appropriate in the form of a compound which contains the latter in a protected form. A protected form of the mercapto group is defined as a compound in which the mercapto group is linked via a disulfide linkage to another mercapto-containing component such as, for example, pyridinethione. It is then possible to cleave off the mercapto-containing component under reducing conditions.

In a preferred procedure, the Bis-Boc-insulin derivative is reacted with a thiol or a reactive component containing a mercapto in protected form, for example a thioalkaneimidate, thiolactone or pyridyldithio ester. The mercapto group is introduced by reacting the N-terminal amino group of the intact or shortened insulin B-chain with a mercapto-containing active ester, it being possible to use, for example, esters of hydroxysuccinimide or of o- or p-nitrophenol.

In a particularly preferred procedure the reactive component used is N-succinimidyl 3-(2-pyridyldithio)-propionate.

Subsequently, the t-butyloxycarbonyl(Boc) protective groups are cleaved off by methods customary in peptide chemistry, for example by treatment with trifluoroacetic acid or an HCl/acetic acid mixture, but preferably trifluoroacetic acid.

The mercapto-containing insulin derivative prepared in the manner described above is now, for the preparation of an insulin derivative of the general formula I, brought into contact with a physiologically tolerated carbon compound which contains mercapto or the mercapto group in protected form. An insulin-S-S-carbon compound complex is prepared by forming a disulfide between insulin and the carbon compound, both of which contain a mercapto group in protected or unprotected form.

In a preferred procedure the physiologically tolerated carbon compound used is a mercapto-containing protein, for example a proteinase inhibitor or mercapto-containing carrier. Alpha$_1$-antitrypsin is used in a particularly preferred process. However, it is also possible to use carriers which initially do not contain a mercapto group in the protected or unprotected form. Before the reaction with insulin containing a mercapto group, carrier substances of this type are reacted with reactive components such as thio-lactones or N-succinimidyl 3-(2-pyridyldithio)propionate (SPDP); reaction with SPDP is particularly preferred.

For the preparation of an insulin derivative of the general formula II, the mercapto-containing insulin derivative prepared in the manner described above is reacted with a physiologically tolerated carbon compound which contains mercapto or the mercapto group in protected form. An insulin-S-S-carbon compound- is prepared by disulfide formation.

In a preferred procedure, the mercapto-containing carbon compound used is, for example, pyridinethione, cysteine, mercaptopropionic acid, mercaptoacetic acid, pyridinethionecarboxylic acid, glutathione, cysteamine, mercaptosuccinic acid or thiamine. In a particularly preferred procedure, use is made of pyridinethione.

An alpha$_1$-antitrypsin-S-S-insulin complex or pyridyl-S-S-insulin complex prepared in the manner described above is particularly distinguished by retaining the biological activity of insulin, being soluble in water even at physiological pH and able to undergo absorption both i.m. and subcutaneously, being protected, in the case of the alpha$_1$-antitrypsin-S-S-insulin complex, from proteolytic inactivation, having a defined stoichiometry between insulin and the physiologically tolerated substance, and having more advantageous pharmacokinetic properties than those of soluble insulin or the long-acting depot insulins.

The pharmacokinetic data of an alpha$_1$-antitrypsininsulin complex for intravenous and subcutaneous administration are shown in Table 1.

The complexes between insulin and alpha$_1$-antitrypsin or pyridinethione prepared in the manner described above can be used for the treatment of metabolic disorders, for example of diabetes mellitus.

These insulin compounds can be administered in the form of agents which have been rendered isotonic with blood, are bactericidal and contain, where appropriate, suitable physiological tolerated additives and stabilizers.

The insulin derivatives can be administered parenterally, for example i.v., i.m., s.c., or by means of an insulin pump.

The examples which follow illustrate the invention.

EXAMPLE 1

Albumin-S-S-insulin complex a) Bis-Boc-insulin 1 g of porcine insulin was dissolved in 37.5 ml of DMF, 9.5 ml of H$_2$O and 2.7 ml of 1 N NaHCO$_3$ solution. Then 930 mg of t-butyloxycarbonyl-hydroxysuccinimide ester dissolved in 2 ml of DMF were added. The mixture was stirred at room temperature for 4 hours, the pH was adjusted to 6.9 with 50% acetic acid, and the solvent was removed in a rotary evaporator. The oily residue was mixed with 10 ml of methanol and then poured into about 250 ml of diethyl ether. The precipitate was removed on a glass frit, washed several times with ethyl acetate and diethyl ether, and dried over KOH and P$_4$O$_{10}$. The dried precipitate was then dissolved in 6 ml of 0.5% NH4HCO3 and subjected to gel filtration on Sephadex ® G-50₅ƒ in 0.5% NH4HCO3. The fractions containing Bis-Boc-insulin were combined and then freeze-dried. Weight: 0.85 g.

b) PDP-Bis-Boc-Insulin

300 μl of N-succinimidyl 3-(2-pyridyldithio)propionate-(SPDP) solution (20 mmol/l in ethanol) were added dropwise, with stirring, to 36 mg of Bis-Boc-insulin derivative in 3 ml of 0.1 mol/l sodium phosphate, 100 mmol/l NaCl, pH 7.5. The solution was left to stand at room temperature for 30 min. The 2-pyridyl-S—S—CH$_2$—CH$_2$—CO—NH—Gly$_1$—insulin-Bis-Boc (PDP-Bis-Boc-insulin) was separated from impurities by gel filtration on Sephadex G-50 in 5 g/l NH4HCO3, pH 8.5, and was then freeze-dried.

c) PDP-Insulin 0 mg of PDP-Bis-Boc-insulin were dissolved in 400 μl of trifluoroacetic acid containing 40 μl of anisole. The solution was left to stand, with exclusion of moisture, at RT for 30 min and at 4° C. for 15 min. The solution was then poured into about 100 ml of cold ether. The precipitate was washed several times with ether, dissolved in 3 ml of 5 g/l NH4HCO3, pH 8.5, and impurities were removed by gel filtration on Sephadex ® G-50. The pure PDP-insulin was then freeze-dried. Following reduction with 0.5 mmol/l dithiothreitol (DTT), an additional band was evident in the UV spectrum at $\lambda_{max}$ 343 nm, this corresponding to free pyridinethione.

d) Albumin-S-S-Insulin 33 mg of mercaptoalbumin were dissolved in 4 ml of 50 mmol/l potassium phosphate, 200 mmol/l NaCl, pH 8.5, and the solution was mixed with 3.3 mg of PDP-insulin in 1 ml of the same buffer. The reaction solution was left to stand at RT for 1 h and at 4° C. for 4 h. The albumin-S-S-insulin complex which had formed was removed from the reactants by gel filtration on Biogel ® P 100. A band corresponding to a product of about 72,000 Dalton was evident in an SDS gel, and, after reduction with DTT, this is split into two bands of about 66,000 Dalton and 6,000 Dalton.

EXAMPLE 2

PDP-insulin was prepared as described in Example 1. 27 mg of alpha$_1$-antitrypsin were dissolved in 2 ml of a solution containing 50 mmol/l potassium phosphate and 0 mmol/l NaCl (pH 8.5) and 25 mmol/l dithiothreitol. The reduction solution was left to stand at 37° C. for 1 h and at 4° C. for 1 h, and then the reducing agent was removed by gel filtration on Sephadex ® G-50 in the same buffer. 27 mg of alpha1-antitrypsin-SH in 6 ml of the above buffer were mixed with 3.2 mg of PDP-insulin in 1 ml of buffer. The treatment and working-up of the complex mixture was carried out as described in Example 1. A band with a MW of about 60,000 Dalton was evident in an SDS gel. After reduction with DTT, this was broken down into 2 bands with molecular weights of about 54,000 and 6,000 Dalton. The purified alpha$_1$-antitrypsin-S-S-insulin complex exhibited inhibiting properties towards proteases such as chymotrypsin, trypsin and elastase.

EXAMPLE 3

An alpha$_1$-antitrypsin-S-S-insulin complex was prepared as in Example 2, replacing porcine insulin by human insulin.

TABLE 1

Rabbit blood glucose level after administration of soluble insulin or alpha$_1$-antitrypsin-insulin complex, as a percentage of the initial level as a function of time

| | intravenous IU/ml/kg | | | | subcutaneous IU/ml/kg | | | |
|---|---|---|---|---|---|---|---|---|
| | 0.5 | | 1.0 | | 0.5 | | 1.0 | |
| t in h | SI | CI | SI | CI | SI | CI | SI | CI |
| 0 | 100 | | 100 | | 100 | | 100 | |
| 0.5 | 20 | 34 | 18 | 32 | 45 | 85 | 45 | 85 |
| 1 | 25 | 40 | 20 | 35 | 42 | 58 | 43 | 58 |
| 2 | 45 | 35 | 42 | 30 | 45 | 52 | 45 | 47 |
| 3 | 80 | 45 | 70 | 40 | 37 | 45 | 43 | 35 |
| 4 | 110 | 65 | 92 | 53 | 52 | 45 | 53 | 32 |
| 5 | 125 | 90 | 108 | 74 | 65 | 50 | 78 | 35 |
| 6 | — | — | — | — | 105 | 55 | 80 | 40 |

SI = soluble insulin
CI = alpha$_1$-antitrypsin-S-S-insulin complex
IU = international insulin unit Each blood glucose level represents the mean of the determinations on four rabbits. It was assumed that a substance containing 1 mg of insulin has the hypoglycemic action of 25 IU of insulin.

EXAMPLE 4

An alpha$_1$-antitrypsin-S-S-insulin complex was prepared as in Example 2, bovine insulin being used in place of porcine insulin.

EXAMPLE 5

Pancreatic trypsin inhibitor (PTI)-S-S-insulin complex

In the first place, PTI was reacted as specified in J. Biol. Chem. 235 (2), 396-404 (1960) with N-acetyl-DL-homocysteine thiolactone. Specifically, a sample of lyophilized, salt-free PTI was dissolved in boiled, distilled water which had been saturated with natural gas. The pH was adjusted to 7.5 and the protein was treated with diisopropylphosporofluoridate. The solution was clarified by centrifugation and the concentration was adjusted to the desired value. Protein concentration was determined routinely by measurements of absorbancy at 282 mμ ($a_s$=20.0, 1% solution. The reaction vessel consisted of a jacketed beaker with a capacity of about 20 ml. Constant temperature water at 25° was circulated through the jacket. For large scale preparations of the protein derivative, a covered wide-mouth jar (250 ml) may be used as the reaction vessel and the reaction may be performed at room temperature. Weighted amounts of N-acetyl-DL-homocysteine thiolactone were added to the protein solution and the reaction vessel such that the final molar concentration of thiolactone was 10 to 15 times larger than the molar concentration of protein. The pH was adjusted and kept at the desired value by the automatic addition of a standardized NaOH solution. Throughout the course of the reaction, the vessel was flushed with a small stream of nitrogen gas saturated with water vapor. At the determination of the reaction, sulfhydryl groups produced by both aminolysis and hydrolysis were blocked by the addition of methylmercury nitrate in an amount which was estimated from the total base consumption of the pH-stat. Finally, the reaction mixture was exhaustively dialyzed for 3 to 4 days against 0.001 m HCl and the protein was lyophilized. An inhibitor containing a mercapto group was obtained. Reaction with PDP-insulin to give the complex was carried out as described in Example 1. The PTI-S-S-insulin complex exhibited inhibitory properties towards plasmin and trypsin. A band with a MW of 12,000 Dalton was evident in a SDS gel.

EXAMPLE 6

Dextran-S-S-insulin complex

Dextran containing amino groups was reacted with N-actyl-DL-homocysteine thiolactone as described in Example 3. The mercapto content per mol of dextran was about 4 mol of mercapto groups. The subsequent reaction with PDP-insulin to give the complex was carried out as described in Example 1.

EXAMPLE 7

Cysteine-S-S-insulin complex

PDP-insulin (25 mg), prepared as described in Example 1 and dissolved in 5 ml of 50 mmol/l sodium phosphate and 150 mmol/l NaCl, pH 5.0, was reacted with 0.75 g of cysteine hydrochloride in 100 μl of the same buffer. The reaction was followed by measurement at 343 nm of the pyridinethione liberated. The reaction product was separated from impurities by gel filtration on Sephadex ® G-$50_{sf}$ in 5 g/l $NH_4HCO_3$, pH 8.3, and was freeze-dried.

EXAMPLE 8

Thiamine-S-S-insulin complex 25 mg of PDP-insulin in 2 ml of 50 mmol/l sodium phosphate, pH 8.0, were treated with 0.7 mg of dithiothreitol. Reaction was then carried out with 3 mg of thiamine tetrahydrofurfuryl disulfide in 2 ml of the above buffer. The reaction product was removed from impurities by gel filtration on Sephadex ® G-$50_{sf}$ in 5 g/l $NH_4HCO_3$, pH 8.3, and was freeze-dried.

The insulin compounds of Examples 5 to 8 showed a hypoglycemic action in the rabbit model.

We claim:

1. An insulin derivative of the formula $$X-Y_1-S-S-Y_2-Z\text{-Insulin}$$

in which $X-Y_1$ is alpha-1-antitrypsin, albumin, pancreatic trypsin inhibitor, dextran containing amino groups, cysteine or thiamine, $Y_2$ is $-CH_2-CH_2-C=O$ or $-CH_2-CH_2-CH(NH\text{-acetyl})-C=O$, S is a sulfur atom, Z is an amino group which is nonessential for the biological activity of insulin, and Insulin denotes the biologically active natural, semi-synthetic or synthetic insulin.

2. An insulin derivative as claimed in claim 1, wherein X is a radical of alpha$_1$-antitrypsin.

3. A method for the treatment of metabolic disorders in a mammal which comprises administering to said mammal an effective amount of a compound of the formula as claimed in claim 1.

4. The method for treatment as claimed in claim 3, wherein the metabolic disorder is diabetes mellitus.

* * * * *